United States Patent [19]

Krass et al.

[11] Patent Number: 4,468,244

[45] Date of Patent: Aug. 28, 1984

[54] HERBICIDALLY ACTIVE BENZOXAZOLYLOXY BENZOATE DERIVATIVES

[75] Inventors: Dennis K. Krass, Canal Fulton; Sidney B. Richter, Fairlawn, both of Ohio

[73] Assignee: PPG Industries, Inc., Pittsburgh, Pa.

[21] Appl. No.: 447,838

[22] Filed: Dec. 8, 1982

[51] Int. Cl.³ .................... C07D 263/54; A01N 43/00
[52] U.S. Cl. ........................................ 71/88; 548/165; 548/221; 548/326; 424/270; 424/272; 424/273 B
[58] Field of Search ............................. 548/221; 71/88

[56] References Cited

U.S. PATENT DOCUMENTS

| | | | |
|---|---|---|---|
| 3,933,841 | 1/1976 | Brenneisen et al. | 548/221 |
| 3,979,437 | 9/1976 | Theissen | 71/115 |
| 4,048,217 | 9/1977 | Rohr | 71/115 |
| 4,063,929 | 12/1977 | Bayer et al. | 71/115 |
| 4,336,057 | 6/1982 | Bieringer et al. | 71/88 |

Primary Examiner—Donald G. Daus
Assistant Examiner—S. A. Gibson
Attorney, Agent, or Firm—Edward J. Whitfield

[57] ABSTRACT

Disclosed are certain herbicidally active benzoxazolyloxy benzoate derivatives, herbicidal compositions containing these compounds and the use of such compounds to control the growth of noxious plants, i.e., weeds.

7 Claims, No Drawings

HERBICIDALLY ACTIVE BENZOXAZOLYLOXY BENZOATE DERIVATIVES

DESCRIPTION OF THE INVENTION

This invention relates to certain benzoxazolyloxy benzoate derivatives of the Formula I:

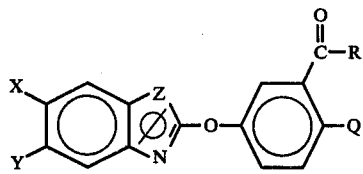

wherein:

Q is halogen (e.g., chlorine, bromine or fluorine), nitro, or cyano;

X and Y are the same or different and represent hydrogen, halogen (e.g., chlorine, bromine, or fluorine), or $C_1$ to $C_4$ alkoxy, $C_1$ to $C_4$ alkyl, $C_1$ to $C_4$ haloalkyl (e.g., trifluoromethyl), nitro or cyano;

Z is oxygen, sulfur, —NH—, or —NR$^6$ where R$^6$ is $C_1$ to $C_3$ alkyl; and

R is —OH, —OM, —OR$^1$, —SR$^1$ or —NR$^2$R$^3$ wherein M is an agronomically suitable ionic species (e.g., sodium, potassium or ammonium);

R$^1$ is $C_1$ to $C_{12}$ alkyl optionally substituted by hydroxy or $C_1$ to $C_{12}$ alkoxy, —R$^4$COOR$^5$, wherein R$^4$ is $C_1$ to $C_3$ alkylene optionally substituted by $C_1$ to $C_4$ alkyl and R$^5$ is hydrogen, $C_1$ to $C_{10}$ alkyl or an agronomically suitable ionic species;

R$^2$ is hydrogen, $C_1$ to $C_{12}$ alkyl or $C_3$ to $C_{12}$ alkenyl;

R$^3$ is hydrogen $C_1$ to $C_{12}$ alkyl, $C_3$ to $C_{12}$ alkenyl, $C_1$ to $C_6$ alkoxy, $C_2$ to $C_6$ alkylcarbamyl or $C_1$ to $C_6$ alkane sulfonyl.

Preferred compounds of the Formula I are those wherein at least one of X or Y is halogen, e.g., chlorine, or trifluoromethyl, Z is oxygen, Q is nitro, and R is —OR$^1$ wherein R$^1$ is —R$^4$COOR$^5$.

Compounds of this invention embodied in the Formula I are believed to be herbicidally active and would be effective in regulating growth of a wide variety of undesirable plants, i.e., weeds, when applied, in herbicidally effective amount, to the growth medium prior to emergence of the weeds or to the weeds subsequent to emergence from the growth medium. The term "herbicidally effective amount" is that amount of compound or mixture of compounds of this invention required to so injure or damage weeds such that the weeds are incapable of recovering following application. The quantity of compound or mixture of compounds of this invention applied in order to exhibit a satisfactory herbicidal effect may vary over a wide range and depends on a variety of factors, such as, for example, hardiness of a particular weed species, extent of weed infestation, climatic conditions, soil conditions, method of application and the like. Typically, as little as one or less pound per acre of compound or mixture of compounds of this invention would be expected to provide satisfactory weed control, although in some instances application rates in excess of one pound per acre, e.g., up to 5 pounds per acre might be required. Of course, the efficacy of a particular compound against a particular weed species may readily be determined by routine laboratory or field testing in a manner well known to the art.

A compound or compounds of this invention may, of course, be used as such or in formulation with agronomically acceptable adjuvants, inert carriers, other herbicides, or other commonly used agricultural compounds, for example, insecticides, fungicides, stabilizers, safeners, fertilizers or the like. The compounds of this invention alone or in formulation with other agronomically used materials are typically applied in the form of dusts, granules, wettable powders, solutions, suspensions, aerosols, emulsions, dispersions or the like in a manner well known to the art. When formulated with other typically used agronomically acceptable materials, the amount of compound or compounds of this invention may vary over a wide range, for example, from about 0.05 to 95 percent by weight on weight of formulation. Typically, such formulations would contain from about 5 to 75 percent by weight of compound or compounds of this invention.

A compound or compounds of this invention are effective in controlling a variety of common broad-leaved and grassy weeds at application rates of only a few grams per acre either pre- or postemergent. Exemplary of weeds that may be effectively controlled by the application of compounds of this invention are barnyard grass (*Echinochloa crusgalli*), crabgrass (*Digitaria sauguinalis*), coffeeweed (*Daubentonia punices*), jimsonweed (*Datura stamonium*), johnsongrass (*Sorghum halepense*), tall morningglory (*Ipomoea purpurea*), wild mustard (*Brassica caber*), teaweed (*Sida Spinosa*), velvetleaf (*Abutilin Theophrasti*), wild oat (*Avena fatua*), yellow foxtail (*Setaria glauca*), yellow nutsedge (*Cyperus esculentus*) and the like.

The Formula I compounds of this invention may be prepared by reacting an appropriately substituted benzoxazole of the Formula II:

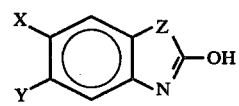

wherin X and Y and Z are as previously defined with an appropriately substituted fluorobenzoic acid of the Formula III:

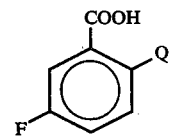

wherein Q is as previously defined, to form a compound of the Formula IV:

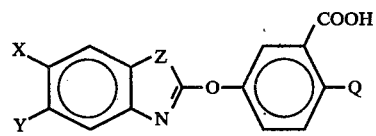

The Formula IV compound is then reacted with an α-halo compound, e.g., α-halocarboxylate of the Formula V:

wherein:

Hal is halogen, e.g., bromine or chlorine; and $R^4$ and $R^5$ are as previously defined to form an invention compound of the Formula I.

The foregoing mode of synthesis is illustrated more specifically as follows:

(a) A reactor is charged with 1.69 grams (0.01 mole) of 5-chlorobenzoxazol-2-one (Formula II Compound), 10 milliliters of dimethylsulfoxide, and 2.76 grams (0.02 mole) of anhydrous potassium carbonate. To this mixture is added 1.85 grams (0.01 mole) of 5-fluoro-2-nitrobenzoic acid (Formula III Compound) in 4 milliliters of dimethylsulfoxide. After stirring at about 75° C. to 80° C. for about 18 hours, the reaction mixture is stripped of solvent and the residue is dissolved in a mixture of methylene chloride and water. The mixture is acidified to pH 2 to 3 with 5 normal hydrochloric acid and the aqueous phase is extracted with methylene chloride. The combined organic phases are washed with water and saturated sodium chloride solution. Filtration and removal of solvent affords 5-(5-chloro-2-benzoxazolyloxy)-2nitrobenzoic acid. (Formula IV Compound);

(b) A reactor is charged with 3.35 grams (0.01 mole) of 5-(5-chloro-2-benzoxazolyoxy)-2-nitrobenzoic acid, prepared as described in part (a), and 30 milliliters of benzene. To this solution is added 1.5 grams (0.011 mole) of ethyl 2-chloro-propionate (Formula V Compound) and 1.67 grams of 1,8-diazabicyclo[5.4.0]undec-7-ene. The reaction mixture is heated at reflux for about 8 hours, cooled, filtered and the filtrate is washed with 0.25 normal sodium hydroxide and saturated sodium chloride solution. Drying over anhydrous magnesium sulfate followed by filtration and removal of solvent affords the desired product, 1-(ethoxycarbonyl)ethyl 5-(5-chloro-2-benzoxazolyloxy)-2-nitrobenzoate.

The manner of preparing a specific compound within the scope of this invention is described in some detail by the foregoing, and it is to be understood that other Formula I compounds can be prepared in like manner by simply varying the choice of starting materials. The compounds of this invention may also be prepared by alternative methods. For example, the compound 1-(ethoxycarbonyl)ethyl 5-(5-chloro-2-benzoxazolyloxy-2-nitrobenzoate, prepared as described hereinabove, may also be prepared as follows:

Substantially equimolar amounts of 2,5-dichlorobenzoxazole and the potassium salt of 2-hydroxy benzoic acid are reacted, in an inert organic solvent, e.g., dimethylsulfoxide, in the presence of acetic acid giving 5-(5-chloro-2-benzoxazolyloxy) benzoic acid. The benzoate is then nitrated by, for example, reaction with a mixture of nitric acid, sulfuric acid and acetic anhydride to give the corresponding 2-nitrobenzoic acid prepared as previously described. The 2-nitrobenzoic acid is then reacted with ethyl 2-chloropropionate, as previously described, giving the desired 1-(ethoxycarbonyl)ethyl 5-(5-chloro-2-benzoxazolyloxy)-2-nitrobenzoate.

Although the invention has been described in some detail with reference to certain embodiments thereof, it is to be understood that it is not intended to be so limited, since many variations may be made therein by those skilled in the art without departing from the spirit and scope thereof as defined in the appended claims.

We claim:

1. A compound of the formula:

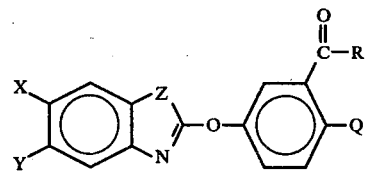

wherein:

Q is halogen, nitro, or cyano;

X and Y are the same or different and represent hydrogen, halogen, $C_1$ to $C_4$ alkyl, $C_1$ to $C_4$ haloalkyl, $C_1$ to $C_4$ alkoxy, nitro or cyano;

Z is oxygen,

R is —OH, —OM, —OR$^1$, —SR$^1$ or —NR$^2$R$^3$ wherein M is an agronomically suitable ionic species;

$R^1$ is $C_1$ to $C_{12}$ alkyl optionally substituted by hydroxy or $C_1$ to $C_{12}$ alkoxy, —R$^4$COOR$^5$, wherein $R^4$ is $C_1$ to $C_3$ alkylene optionally substituted by $C_1$ to $C_4$ alkyl and $R^5$ is hydrogen, $C_1$ to $C_{10}$ alkyl or an agronomically suitable ionic species;

$R^2$ is hydrogen, $C_1$ to $C_{12}$ alkyl or $C_3$ to $C_{12}$ alkenyl;

$R^3$ is hydrogen $C_1$ to $C_{12}$ alkyl, $C_3$ to $C_{12}$ alkenyl, $C_1$ to $C_6$ alkoxy, $C_2$ to $C_6$ alkylcarbamyl or $C_1$ to $C_6$ alkane sulfonyl.

2. A compound of claim 1 wherein at least one of X or Y is halogen or trifluoromethyl.

3. A compound of claim 1 wherein Z is oxygen.

4. A compound of claim 1 wherein Q is nitro.

5. A compound of claim 1 wherein R is —OR$^1$ and $R^1$ is —R$^4$COOR$^5$.

6. In a method of controlling weed growth wherein a herbicidally effective amount of a herbicide is applied either to the growth medium prior to emergence of the weeds therefrom or the weeds subsequent to their emergence from the growth medium wherein the improvement resides in using as the herbicide compound or mixture of compounds defined in claim 1.

7. A herbicidal composition containing an inert carrier and a herbicidally effective amount of a compound or mixture of compounds defined in claim 1.

* * * * *